United States Patent [19]

Yarborough

[11] Patent Number: 4,983,380
[45] Date of Patent: Jan. 8, 1991

[54] COMPOSITION FOR TREATMENT OF TEETH AND METHOD OF USE

[76] Inventor: David K. Yarborough, 3705 Northcote Dr., Birmingham, Ala. 35223

[21] Appl. No.: 406,418

[22] Filed: Sep. 11, 1989

[51] Int. Cl.⁵ .......................... A61K 7/18; A61K 7/20; A61K 33/40
[52] U.S. Cl. .......................... 424/52; 424/53; 424/616; 424/613; 433/215
[58] Field of Search .................... 424/52, 53, 616, 613; 106/178; 433/215

[56] References Cited

U.S. PATENT DOCUMENTS

| | | | |
|---|---|---|---|
| 2,021,131 | 11/1935 | McDaniel | 424/673 |
| 2,923,649 | 11/1960 | Todd | 106/178 |
| 3,337,412 | 8/1967 | Elbroder | 424/673 |
| 3,576,776 | 4/1971 | Muszik | 106/178 |
| 3,960,584 | 6/1976 | Savage | 106/178 |
| 4,128,631 | 12/1978 | Lundmark | 514/785 |
| 4,165,368 | 8/1979 | Gaffar | 424/673 |
| 4,267,167 | 5/1981 | Weitzman et al. | 424/673 |
| 4,312,675 | 1/1982 | Pickens et al. | 106/178 |
| 4,411,889 | 10/1983 | Caslansky et al. | 424/673 |
| 4,469,627 | 9/1984 | Trombone | 106/178 |
| 4,502,888 | 3/1985 | Leng et al. | 106/178 |
| 4,528,180 | 7/1985 | Schaeffer | 424/616 |
| 4,650,670 | 3/1987 | Callingham et al. | 424/DIG. 5 |
| 4,661,070 | 4/1987 | Friedman | 433/215 |
| 4,687,663 | 8/1987 | Schaeffer | 424/53 |
| 4,781,923 | 11/1988 | Pellico | 424/616 |
| 4,788,052 | 11/1988 | Ng et al. | 424/616 |
| 4,828,113 | 5/1989 | Friedland et al. | 206/570 |
| 4,839,156 | 6/1989 | Ng et al. | 424/616 |
| 4,839,157 | 6/1989 | Ng et al. | 424/53 |
| 4,849,213 | 7/1989 | Schaeffer | 424/616 |
| 4,895,721 | 1/1990 | Drueker | 424/616 |
| 4,910,224 | 3/1990 | Habib et al. | 514/558 |

*Primary Examiner*—Shep K. Rose
*Attorney, Agent, or Firm*—Jennings, Carter, Thompson & Veal

[57] ABSTRACT

A mucroprotectant gelatin which forms a protective coating on the mucous membranes of the mouth is provided for use with active ingredients for treating the teeth. The active ingredient may be aqueous hydrogen peroxide solution or fluoride. When hydrogen peroxide is used as a bleaching agent the mucoprotectant prevents the caustic bleaching agent from damaging the gums. The bleaching agent and the mucoprotectant are stored in separate containers and are custom mixed by a supervising dentist and given to the patient in a dispenser so that the resulting slurry may be used in a personalized vacuformed mouthpiece. The treatment may last from several minutes to several hours.

19 Claims, 1 Drawing Sheet

COMPOSITION FOR TREATMENT OF TEETH AND METHOD OF USE

FIELD OF THE INVENTION

The present invention relates generally to oral hygiene and more specifically to the area of cosmetic oral hygiene. In even greater particularity the present invention relates to bleaching the teeth and to protecting the adjacent gingival tissues while doing so. Still more particularly the present invention may be described as a mucoprotectant gel used with hydrogen peroxide to bleach the teeth and protect the mucous membranes.

BACKGROUND OF THE INVENTION

The cosmetic whitening of the teeth has been a prevalent concern of the modern consumer. Traditionally abrasives and bleaches have been used to effectuate the desired whitening. One of the agents used by dentists for in-office cosmetic bleaching has been hydrogen peroxide. While hydrogen peroxide is a very safe chemical in dilute quantities it is very caustic and will cause severe tissue damage at higher concentrations. Thus, its use has heretofore been limited to controlled use in the dentist's office. Recently, dentists have attempted to bleach teeth using a vacuformed mouthpiece which fits over the teeth and adjacent tissue with a dilute hydrogen peroxide gel (1½% hydrogen peroxide). the technique is laudable, the continued exposure of the mucous membranes of the mouth to hydrogen peroxide oft en seems to result in oral irritation which necessitates discontinuation of the treatment. Therefore a need exists for a means for protecting the gum tissues while permitting hydrogen peroxide to contact the teeth.

SUMMARY OF THE INVENTION

It is an object of the present invention to provide an effective means to protect the gums from the caustic action of relatively concentrated hydrogen peroxide without deterring the effectiveness of the hydrogen peroxide bleaching agent for the teeth.

Yet another object of the invention is to provide a means for the patient to safely bleach his teeth at home yet under the dentist's supervision.

Still another object of the invention is to provide a means for bleaching of vital and non-vital teeth as well as bonded surfaces using a mouthpiece.

A further object of the invention is to provide a fluoride treatment to the teeth which may also be bleached.

These and other objects and advantages of my invention are advantageously accomplished using a vacuformed mouthpiece and a concentrated hydrogen peroxide oxidizer and a gelatinous mucoprotectant which forms a hydrophobic coating on the mucous membranes of the mouth to prevent the hydrogen peroxide from attacking these surfaces, yet which does not form such a protective coating on the teeth. My gelatinous mucoprotectant comprises sodium stearate USP, a gelling agent, glycerine, and water with the amount of water or glycerin included varying in an inverse relationship. The sodium stearate USP combines with the hydrogen peroxide to form stearic and palmitic acids which are readily deposited on the mucous membranes to form a protective barrier.

BRIEF DESCRIPTION OF THE DRAWINGS

The appended drawings are illustrative of the use of my compound and form a portion of this disclosure, wherein.

DESCRIPTION OF A PREFERRED EMBODIMENT

As noted hereinabove hydrogen peroxide is an effective whitener of teeth and bonded dental material, yet it is caustic to the adjacent tissues. Therefore, to enable the long-term use of hydrogen peroxide in a loosely supervised, at home, treatment regime requires the use of a mucoprotectant, i.e. a protective coating on the mucous membranes, which will prevent damage to the gum tissues. In my composition, the ingredient which appears to function as the mucoprotectant is sodium stearate USP.

Sodium stearate USP is actually a mixture of sodium stearate (oxtadeconoic acid, sodium salt) and sodium palmitate (hexodecanoic acid, sodium salt) wherein the sodium stearate content is at least 40% by weight. Both sodium stearate and sodium palmitate are water soluble and aqueous solutions of these salts are alkaline. Alcoholic solutions are neutral due to hydrolysis. Stearic acid and palmitic acid, in contrast, are not water soluble.

In my composition I use sodium stearate USP in a gelatinous carrier including water, glycerine, and a gelling agent. Thus a gelatinous mucoprotectant is formed which contains by weight: about 39% glycerine; about 55% water; about 1% sodium stearate USP; and about 5% gelling agent or binder. Additionally, I may use a small amount of fluoride such as sodium fluoride USP. The binder material is a cellulose type binder and although many may be suitable, the binders which have been experimentally verified are listed in tables 1 and 2.

TABLE 1

|  | Percent | Range |  |
|---|---|---|---|
| Glycerine (99%) | 38.85% | 25.00% to | 50.00% |
| Water | 55.21% | 71.17% to | 41.40% |
| Sodium stearate USP | 1.07% | 0.50% to | 1.50% |
| Sodium fluoride USP | 0.09% | 0.08% to | 0.10% |
| Hydroxyethylcellulose | 3.58% | 2.50% to | 5.00% |
| Methylcellulose | 1.19% | 0.75% to | 2.00% |

TABLE 2

|  | Percent | Range |  |
|---|---|---|---|
| Glycerine (99%) | 38.85% | 25.00% to | 50.00% |
| Water | 55.21% | 71.22% to | 40.40% |
| Sodium stearate USP | 1.07% | 0.50% to | 1.50% |
| Sodium fluoride USP | 0.09% | 0.08% to | 0.10% |
| Carboxymethylcellulose | 4.30% | 3.00% to | 6.00% |
| Powdered gelatin | 0.24% | 0.10% to | 1.00% |
| Pectin | 0.24% | 0.10% to | 1.00% |

Figure 3:
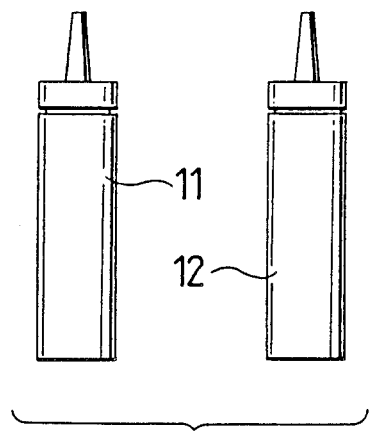
FIG. 3 is a pictorial representation of my composition in its storage containers.

The gelatinous mucoprotectant made in accordance with the above formula can be a stand-alone treatment for the teeth if the fluoride is included, however the fluoride does not enhance whitening the teeth. The whitening agent is an aqueous solution of hydrogen peroxide having an hydrogen peroxide concentration of between about 10% to 35% by weight. Separately the aqueous hydrogen peroxide solution and the gelatinous mucoprotectant can be stored in containers 11 and 12 of FIG. 3 for an indeterminate amount of time. Note, that hydrogen peroxide in this concentration cannot be introduced directly into the oral cavity without deleterious results.

Figure 1:
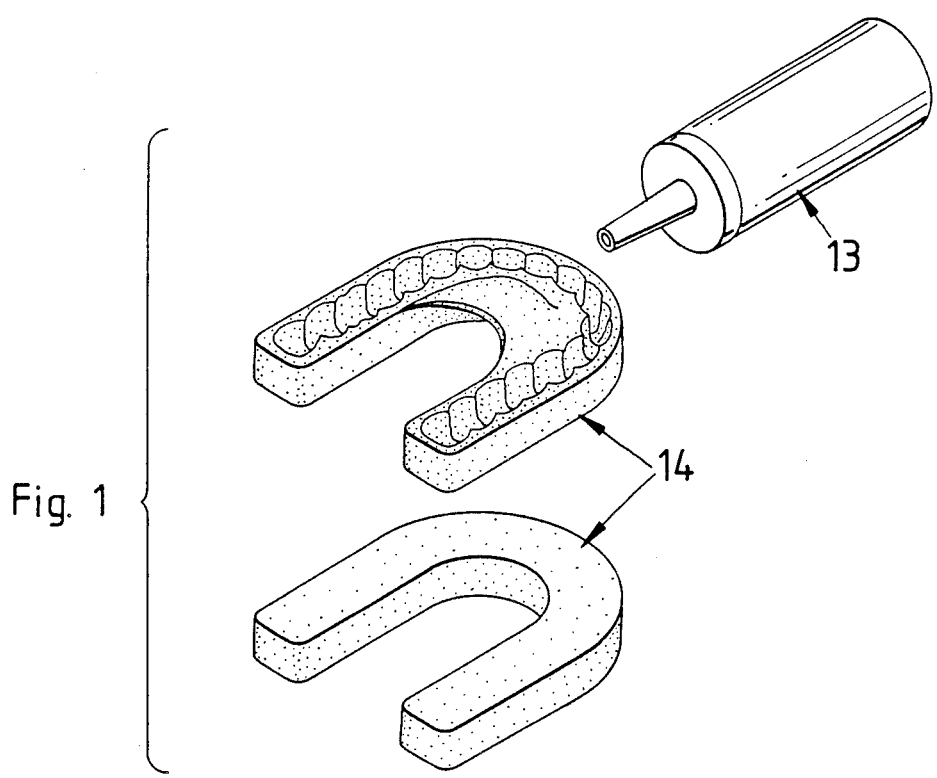
FIG. 1 is a perspective view of a vacuformed mouth guard and a dispenser container for my combined composition.

Rather, the aqueous hydrogen peroxide solutions and the gelatinous mucoprotectant are combined in a dispensing container 13, shown in FIG. 1, at a ratio of about 1 part aqueous hydrogen peroxide solution to from about 2 to 5 or more parts gelatinous mucoprotectant. It may be seen that the hydrogen peroxide content will thus vary from about 2% by weight to about 15% by weight of the combination, with the concentration to be used to be selected by the dentist for each patient.

Figure 2:
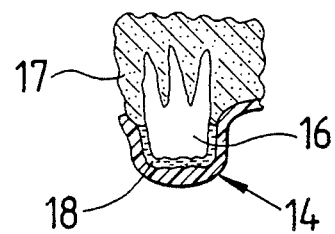
FIG. 2 is a sectional view of the mouth guard in situ about the teeth with my composition in contact therewith.

Although the exact modality is not clearly understood, when the combination in dispenser 13 is placed in a mouthpiece 14 and inserted in the mouth about the teeth 16 and adjacent gums 17, as shown in FIG. 2, a protective coating having an affinity for the mucous membranes underlying the membranes attaches to these membranes but does not attach to the teeth. This coating has a hydrophobic characteristic in that it does not permit the hydrogen peroxide to reach the gum tissue, thus no caustic effects of the hydrogen peroxide occur on these gingival tissues. It is believed that the addition of the acidic hydrogen peroxide to the gelatinous mucoprotectant form stearic acid and palmitic acid in situ. In this state they are readily deposited on the mucous membranes to block the hydrogen peroxide.

In actual practice, the dentist maintains a quantity of gelatinous mucoprotectant and aqueous hydrogen peroxide solution in bulk as in containers 11 and 12. When a patient desires a whitening treatment, the dentist mixes the mucoprotectant and hydrogen peroxide in the desired ratio in dispensing container 13 and makes a vacuformed mold 14 of the patient's teeth. When the mucoprotectant and the hydrogen peroxide are mixed, the resulting slurry 18 has a shelf-life of about three days, thus the patient is instructed to place the slurry in the mouthpiece 14 and position it over the teeth. The mouthpiece 14 with the slurry 18 may normally be retained in the mouth for as little as twenty minutes or as long as several hours without adverse effects.

It is also noteworthy to mention that hydrogen peroxide bleaching oftentimes increase the porosity of the tooth thus making the tooth somewhat more sensitive. This may be remedied to some extent by including fluoride in the gelatinous mucoprotectant as shown in the above tables so that the fluoride aids in remineralization of the tooth as the tooth is bleached. The mucoprotectant with the fluoride additive may also be used in the absence of the hydrogen peroxide solution as a fluoride treatment for the teeth. Thus, beneficial results may be obtained using my mucoprotectant gel with either a hydrogen peroxide bleaching solution or a fluoride remineralization solution. Of course, it may also be desirable to add a flavoring in small percentages, however such additives would not constitute a part of this invention.

While I have shown my invention in various forms, it will be obvious to those skilled in the art that it is not so limited but is susceptible of various changes and modifications without departing from the spirit thereof.

What I claim is:

1. A composition of matter for oral application to the teeth and adjacent gingival tissues comprising:
   (a) a predetermined amount of an active ingredient for the beneficial treatment of the teeth selected from the group of hydrogen peroxide and mixtures thereof with fluoride; and
   (b) a gelatinous mucoprotectant water soluble sodium stearate gel for preventing irritation of the mucous membranes of the mouth by forming a hydrophobic coating thereon.

2. A composition of matter as defined in claim 1 wherein said active ingredient is a hydrogen peroxide solution having a hydrogen peroxide concentration between 10% to 35% by weight.

3. A composition of matter as defined in claim 2 wherein said gelatinous mucoprotectant water soluble sodium stearate gel comprises sodium stearate, a cellulose emulsifier, and water.

4. A composition of matter as defined in claim 3 wherein said sodium stearate comprises about 0.50% to about 1.5% by weight of said mucoprotectant water soluble sodium stearate gel.

5. A composition of matter as defined in claim 4 wherein said cellulose emulsifier comprises hydroxyethylcellulose of about 2.5% to about 5% by weight of said mucoprotectant water soluble sodium stearate gel and methylcellulose of about 0.75% to about 2.00% by weight of said mucoprotectant water soluble sodium stearate gel.

6. A composition as defined in claim 5 further comprising water of about 41% to about 71% by weight of said mucoprotectant water soluble sodium stearate gel and glycerine of about 25% to about 50% by weight of said mucoprotectant said glycerin and water having inverse relation in the quantity contained in said mucoprotectant water soluble sodium stearate gel.

7. A composition of matter as defined in claim 4 wherein said cellulose emulsifier comprises carboxymethylcellulose of about 3% to about 6% by weight of said mucoprotectant water soluble sodium stearate gel, powdered gelatin and pectin, each of about 0.10% to 1.00% by weight of said mucoprotectant water soluble sodium stearate gel.

8. A composition as defined in claim 7 further comprising water of about 41% to about 71% by weight of said mucoprotectant water soluble sodium stearate gel and glycerine of about 25% to about 50% by weight of said mucoprotectant water soluble sodium stearate gel said glycerin and water having inverse relation in the ,quantity contained in said mucoprotectant water soluble sodium stearate gel.

9. A composition of matter as ,defined in claim 2 wherein said mucoprotectant water soluble sodium stearate gel comprises sodium stearate, a gelling agent, water, and glycerine.

10. A composition of matter as defined in claim 2 wherein said mucoprotectant, water soluble sodium stearate gel comprises sodium stearate of about 0.50% to about 1.5% by weight; a gelling agent of about 3.2% to about 8.0% by weight; water of about 41% to about 71% by weight; and the balance glycerine.

11. A composition of matter as defined in claim 10 wherein said hydrogen peroxide is contained in an aqueous solution of about 10% to 35% hydrogen peroxide.

12. A composition of matter as defined in claim 11 wherein said hydrogen peroxide makes up between about 2.0% to about 15% by weight of said composition.

13. A composition as defined in claim 11 wherein said aqueous solution is combined with said gelatinous mucoprotectant water soluble sodium stearate gel at a ratio of between about 1:2 to about 1:5 by weight.

14. A composition of matter as defined in claim 10 further comprising sodium fluoride in an amount of about 0.08% to about 0.10% by Weight of said mucoprotectant water soluble sodium stearate gel.

15. A composition of matter as defined in claim 1 wherein said active ingredient, includes sodium fluoride.

16. A composition of matter as defined in claim 15 wherein said mucoprotectant water soluble sodium stearate gel comprises sodium stearate of about 0.50% to about 1.5% by weight; a gelling agent of about 3.2% to about 8.0% by weight; water of about 41% to about 71% by weight; and the balance glycerine.

17. A mucoprotectant gel for preventing irritation of oral mucous membranes during the application of any aqueous hydrogen peroxide solution having a hydrogen peroxide concentration between 10% to 35% by weight to the teeth comprising sodium stearate, a gelling agent, water, and glycerine.

18. A mucoprotectant gel as defined in claim 17 wherein said mucoprotectant comprises sodium stearate of about 0.50% to about 1.5% by weight; a gelling agent of about 3.2% to about 8.0% by weight; water of about 41% to about 71% by weight; and the balance glycerine.

19. A mucoprotectant gel as defined in claim 18 further comprising sodium fluoride in an amount of about 0.08% to about 0.10% by weight of said mucoprotectant.

* * * * *